United States Patent [19]

Chen et al.

[11] Patent Number: 5,397,488

[45] Date of Patent: Mar. 14, 1995

[54] OXIDATIVELY STABLE ESTERS DERIVED FROM DIAMONDOIDS TOTALLY HYDROXYLATED AT THE BRIDGEHEADS

[75] Inventors: Catherine S. H. Chen, Berkeley Heights; Suzanne E. Schramm, Robinsville; Steven E. Wentzek, East Brunswick, all of N.J.

[73] Assignee: Mobil Oil Corporation, Fairfax, Va.

[21] Appl. No.: 164,275

[22] Filed: Dec. 9, 1993

[51] Int. Cl.$^6$ ............................................. C10M 129/72
[52] U.S. Cl. ................................... 252/56 S; 252/57; 560/190; 560/204
[58] Field of Search ..................... 252/57, 56 R, 56 S; 560/190, 204

[56] References Cited

U.S. PATENT DOCUMENTS

| | | | |
|---|---|---|---|
| 3,648,531 | 3/1972 | Duling et al. | 74/200 |
| 3,671,598 | 6/1972 | Moore | 260/666 M |
| 3,671,600 | 6/1972 | Moore | 260/666 M |
| 3,793,203 | 2/1974 | Driscoll et al. | 252/56 R |
| 3,849,473 | 11/1974 | Inamoto et al. | 252/56 R |
| 3,903,001 | 9/1975 | Gates et al. | 252/32.7 E |
| 3,966,624 | 6/1976 | Duling et al. | 252/52 R |
| 3,972,243 | 8/1976 | Driscoll et al. | 74/200 |
| 4,041,086 | 8/1977 | Moore et al. | 260/648 F |
| 4,043,927 | 8/1977 | Duling et al. | 252/52 R |
| 4,180,466 | 12/1979 | Newingham et al. | 252/48.6 |
| 4,786,427 | 11/1988 | Dare-Edwards | 252/56 R |
| 4,913,794 | 4/1990 | Le et al. | 208/18 |
| 4,963,292 | 10/1990 | Honna et al. | 252/56 S |
| 5,085,792 | 2/1992 | Narihiko et al. | 252/79 |

OTHER PUBLICATIONS

Stetter; Krause, Justus Liebgo Ann. Chem., 717 1968, 60, Coden: JLACBF.

14 *Kirk–Othmer Encyclopedia of Chemical Technology* 489 (Wiley, 1981).

*Primary Examiner*—Jacqueline V. Howard
*Attorney, Agent, or Firm*—Alexander J. McKillop; Dennis P. Santini; Robert B. Furr, Jr.

[57] ABSTRACT

The invention provides a composition comprising Formula I as shown below and at least one selected from the group consisting of Formulae II, III, IV, and V as shown below:

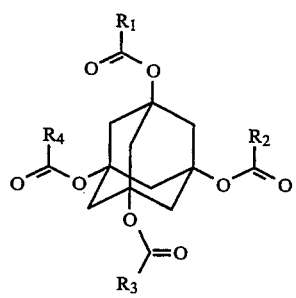

Formula I

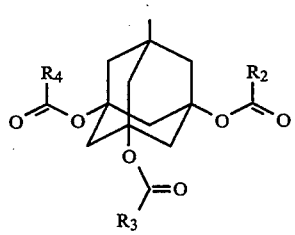

Formula II

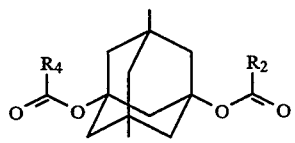

Formula III

Formula IV (Abstract continued on next page.)

Formula V wherein $R_1$, $R_2$, $R_3$, and $R_4$ are the same or different, and comprise alkyl groups containing no tertiary carbon and having from about 4 to about 15 carbon atoms. The composition of the invention is useful as a lubricant stock. A method for synthesizing the composition is also disclosed.

38 Claims, 9 Drawing Sheets

NMR SPECTRA OF THE HYDROXY ADAMANTANES

OXIDATIVELY STABLE ESTERS DERIVED FROM DIAMONDOIDS TOTALLY HYDROXYLATED AT THE BRIDGEHEADS

FIELD OF THE INVENTION

This invention relates to carboxyric acid per-esters of perhyroxy diamondoids. More particularly, the invention relates to per-esterified diamondoids including alkyl substituted and unsubstituted adamantanes, and lubricant compositions containing the same.

BACKGROUND OF THE INVENTION

Efforts to improve upon the performance of natural mineral oil based lubricants by the synthesis of oligomeric hydrocarbon fluids have been the subject of important research and development in the petroleum industry for at least fifty years and have led to the relatively recent market introduction of a number of superior synthetic lubricants, for example, polyalphaolefins. In terms of lubricant property improvement, the thrust of the industrial research effort on synthetic lubricants has been toward fluids exhibiting useful viscosities over a wide range of temperature, i.e., improved viscosity index, while also showing lubricity, thermal and oxidative stability and pour point equal to or better than mineral oil. Viscosity index (VI) is the most common measure that is applied to the decrease in viscosity of petroleum oils with increasing temperature. A series of Pennsylvania oils exhibiting relatively small change in viscosity with changing temperature is arbitrarily assigned a VI of 100, whereas a series of Gulf Cost oils whose viscosities change relatively greatly is assigned a VI of 0. From the viscosity measurements at 40° and 100° C., the VI of any oil sample can be obtained from detailed tables published by the ASTM (ASTM D-2270). 14 Kirk-Othmer Encyclopedia of Chemical Technology 489 (Wiley, 1981). U.S. Pat. No. 4,913,794 to Le et al. teaches a method for improving the viscosity index of a lubricant stock and is incorporated herein by reference for its discussions of viscosity index and lubricant upgrading processes.

U.S. Pat. No. 3,671,598 to Moore relates to the isomerization of adamantane-containing compounds in the presence of sulfuric acid to provide useful traction fluids.

U.S. Pat. No. 3,648,531 to Duling et al. teaches a traction drive containing a fluid comprising an alkyladamantane dimer or an alkyladamantanol dimer.

U.S. Pat. No. 3,671,600 to Moore teaches ethylation of an adamantane nucleus in the presence of a strong acid and $BF_3$ etherate.

U.S. Pat. No. 3,793,203 to Driscoll et al. discloses polyolefins, paraffins, and polar compounds containing a gemdialkyl substituted back-bone structure which are useful as traction fluids.

U.S. Pat. No. 3,903,001 to Gates et al. and U.S. Pat. No. 4,180,466 to Newingham et al. teach synthetic lubricants for limited slip differentials.

U.S. Pat. No. 3,966,624 to Driscoll et al. relates to a hydrogenated polymeric traction fluid containing a light olefin oligomer and at least one saturated adamantane compound.

U.S. Pat. No. 3,972,243 to Driscoll et al. relates to polyolefins, paraffins, and polar compounds containing a gem-structured backbone structure which are useful as lubricant additives and traction fluid components.

Fluorinated adamantanes are taught in U.S. Pat. No. 4,041,086 to Moore et al. Adamantane-containing ethers are shown in U.S. Pat. No. 4,043,927 to Duling et al.

Ester compounds containing one or two cyclic or bicyclic alkanes which are useful as traction fluids are disclosed in U.S. Pat. No. 4,786,427 to Dare-Edwards.

U.S. Pat. No. 5,085,792 to Narihiko et al. relates to a synthetic traction fluid comprising two substituted cyclohexane nuclei connected through an ester linkage.

U.S. Pat. No. 4,963,292 to Honna et al. discloses a higher carboxylic acid triester of adamantane triol which is said to be a useful ingredient in synthetic lubricants.

SUMMARY OF THE INVENTION

This invention provides novel diamondoid esters which are useful as thermally and oxidatively stable components of synthetic lubricants. The adamantane esters of the invention have structures as shown below in Formulae I through V:

Formula I

Formula II

Formula III

Formula IV

Formula V wherein $R_1$, $R_2$, $R_3$, and $R_4$ are the same or different, and comprise alkyl groups containing no tertiary carbons, and having from about 2 to about 15 carbon atoms, preferably from about 4 to about 11 carbon atoms, more preferably from about 5 to about 9 carbon atoms. In one preferred embodiment, $R_1$, $R_2$, $R_3$, and $R_4$ are carboxylic acids such as n-$C_9H_{19}$ COOH and —$CH_2COOH$.

The invention further comprises a mixture of esterified diamondoids which is particularly useful as a high performance synthetic lubricant base stock due to its excellent thermal and oxidative stability. In another preferred embodiment, the invention comprises per-esterified adamantane containing ester groups at each of the 1-, 3-, 5-, and 7- bridgehead carbon positions. The preferred mixture of the invention contains at least one compound of Formula I and at least one compound selected from the group consisting of the compounds of Formulae II, III, IV, and V.

BRIEF DESCRIPTION OF THE DRAWINGS

FIGS. 5 and 6 shows the disappearance of tertiary carbons and the appearance of additional quaternary carbons and hydroxyl groups.

FIGS. 6 and 7 shows the disappearance of hydroxyl groups and the appearance of ester groups upon esterification of the mixture.

DETAILED DESCRIPTION

This invention provides novel per-esterified diamondoid compounds, mixtures of diamondoid esters containing per-esterified diamondoids, and a two-step method for making the per-esters and the mixed esters. The per-esterified diamondoid compounds and the mixed esters are useful as lubricant stocks due to their lubricity as well as their thermal/oxidative stability.

Feedstocks useful in the present invention include substituted or unsubstituted adamantane, and a mixture of alkyl-substituted adamantane compounds is preferred. Examples of particularly preferred substituted adamantane starting materials include adamantane, methyladamantane, dimethyladamantane, trimethyladamantane, and the following adamantanes with at least one bridgehead position unsubstituted: tetra-, penta-, hexa-, hepta-, and octa-methyladamantanes.

The first step of the two-step synthesis method of the present invention hydroxylates the tertiary adamantane bridgehead positions as well as the other tertiary carbons in the molecule. For example, 2-methyladamantane has four bridgehead tertiary carbons and one non-bridgehead tertiary carbon at the 2-position. Suitable oxygen donors include the inorganic persulfates, and OXONE brand monopersulfate compound (formula: $2KHSO_5.KHSO_4.K_2SO_4$, commercially available from E. I. Du Pont de Nemours and Company, 1007 Market Street, Wilmington, Del., 19898) is particularly preferred.

The amount of oxygen donor used in the first step typically ranges from about 1 to about 10 moles per mole of adamantane bridgehead substituent groups for oxidation, preferably from about 2 to about 4 moles per mole of tertiary carbons.

The first reaction step of the synthesis process of the present invention is preferably promoted by an oxygen carrier. Useful oxygen carriers include acetone and 1,1,1-trifluoroacetone, and 1,1,1-trifluoroacetone is a particularly preferred oxygen carrier. The oxygen carrier is typically present in excess, and the amount of oxygen carrier is not critical. Useful amounts of oxygen carrier typically fall within the range of from about 1 to about 2 moles of oxygen carrier per mole of oxygen donor.

Table I shows useful oxidation conversion conditions. These conditions are not considered critical. Particularly, the oxidation reaction appears to proceed extremely rapidly and while short reaction times may work acceptably well, longer reaction times may be preferred to assure that the oxidation reaction is complete.

TABLE I

| Oxidation Conversion Conditions | | |
|---|---|---|
| | Useful | Preferred |
| Temperature | −20 to +20° C. | −10 to +10° C. |
| Pressure | approximately atmospheric | — |
| Pot Reaction Time | 0.1 to 24 hours | 4 to 16 hours |

The second step of the two-step synthesis method of the present invention esterifies the hydroxylated adamantane tertiary carbons with at least one esterification agent selected from the group consisting of the n-alkanoic acids and the neoacids. Suitable n-alkanoic acids include butyric acid, valeric acid, hexanoic acid, heptanoic acid, octanoic acid (caprilic acid), nonanoic acid (pelargonic acid), decanoic acid (capric acid), dodecanoic acid (lauric acid), and hexadecanoic acid (palmitic acid).

Suitable neoacids include trimethylacetic acid (pivalic acid), α,α-dimethylalkanoic acids or the corresponding methyl esters if a transesterifiation technique is employed. Methyl decanoate and methyl hexanoate are particularly preferred esterification agents.

The esterification step is preferably promoted by an esterification catalyst. Suitable esterification catalysts include strong acids or bases when acids are used in the esterification step. Titanium (IV) alkoxides are preferred catalysts when methyl esters of alkanoic acids are used in the ester interchange step, and titanium (IV) isopropoxide (commercially available from Aldrich, 1001 West Saint Paul Avenue, Milwaukee, Wis. 53223) is particularly preferred.

The amount of esterification agent used in the second step typically ranges from about 1.5 to about 10 moles per mole of hydroxyl groups for esterification, preferably from about 2 to about 4 moles per mole of hydroxyl group.

The amount of esterification catalyst typically ranges from about 0.001 to about 0.1 moles of esterification catalyst per mole of adamantyl hydroxyl group, preferably from about 0.005 to about 0.2 moles of esterification catalyst per mole of adamantyl hydroxyl group.

Table II shows useful esterification conversion conditions. The esterification reaction may also proceed in an acceptable manner at tempertures and pressures outside the disclosed reaction conditions, and therefore the disclosed conditions are not considered critical.

TABLE II

| Esterification Conversion Conditions | | |
| --- | --- | --- |
| | Useful | Preferred |
| Temperature | 80 to 160° C. | 100 to 140° C. |
| Pressure | approximately atmospheric | — |
| Pot Reaction Time | 0.1 to 24 hours | 4 to 16 hours |

The esterified diamondoid compounds of the invention may be used neat, or may be admixed with a standard additive package including oxidation inhibitors, extreme-pressure antiwear additives, viscosity index improvers, coantioxidants, antiwear agents, and the like. Examples of such additives include, but are not limited to, phenates, sulfonates, succinimides, zinc dialkyl or diaryl dithiophosphates, and the like.

The compounds of this invention are useful as synthetic lubricant basestocks. These compounds may optionally be admixed with mineral or other synthetic lubricating oils, for example, polyalphaolefins, to improve thermal and oxidative stability of the mixture in comparison with the unmixed mineral or synthetic lubricating oil. The per-esters of Formula I (as defined herein) are particularly preferred blending stocks for improving the thermal and oxidative stability of a lubricant basestock containing less stable components. The compounds of the invention are also useful as grease components. In a preferred embodiment, the composition of this invention is the principal lubricating fluid of the grease composition. Alternatively, the compounds of this invention may be admixed with lubricating oils or grease vehicles having any suitable lubricating viscosity range, for example, from about 45 SSU at 100° F. to about 6000 SSU at 100° F., and preferably from about 50 to about 250 SSU at 210° F. These oils may have viscosity indexes ranging to 100 or higher. The average molecular weight of oils useful for blending with the compounds of the present invention can range from about 250 to about 800.

Where a compound of the present invention is employed as a lubricating oil in a grease, the lubricating oil is generally used in an amount sufficient to balance the total grease composition, after accounting for the desired quantity of the thickening agent, and other additive components included in the grease formulation. A wide variety of materials can be employed as. thickening or gelling agents. These can include any of the conventional metal salts or soaps, such as calcium, or lithium stearates, or hydroxystearates, which are dispersed in the lubricating vehicle in grease-forming quantities in an amount to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt and dissolve when used at the required temperature within a particular environment; however, in all other respects, any material which is normally employed for thickening or gelling hydrocarbon fluids for forming grease can be used in preparing an improved grease in accordance with the present invention.

The compositions of this invention, when formulated into commercial lubricants, are preferably the principal component of the commercial lubricant compositions due to their inherently high thermal and oxidative stability.

In instances where other synthetic oils, or other synthetic oils employed as the vehicle for the grease, are desired as blending components for use with the compounds of the present invention, various synthetic oils may be used successfully. The compounds of the present invention have superior thermal and oxidative stability and are therefore desirable blending components for improving the overall thermal and oxidative stability of a lubricant basestock containing less stable compounds. Typical synthetic oil vehicles which can be improved by adding the compounds of this invention include polyisobutylenes, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes, and silicones (polysiloxanes) and alkyl-substituted diphenyl esters typified by a butyl-substituted bis(p-phenoxy phenyl) ether, and phenoxy phenylethers.

EXAMPLES

Example 1

Figure 1:
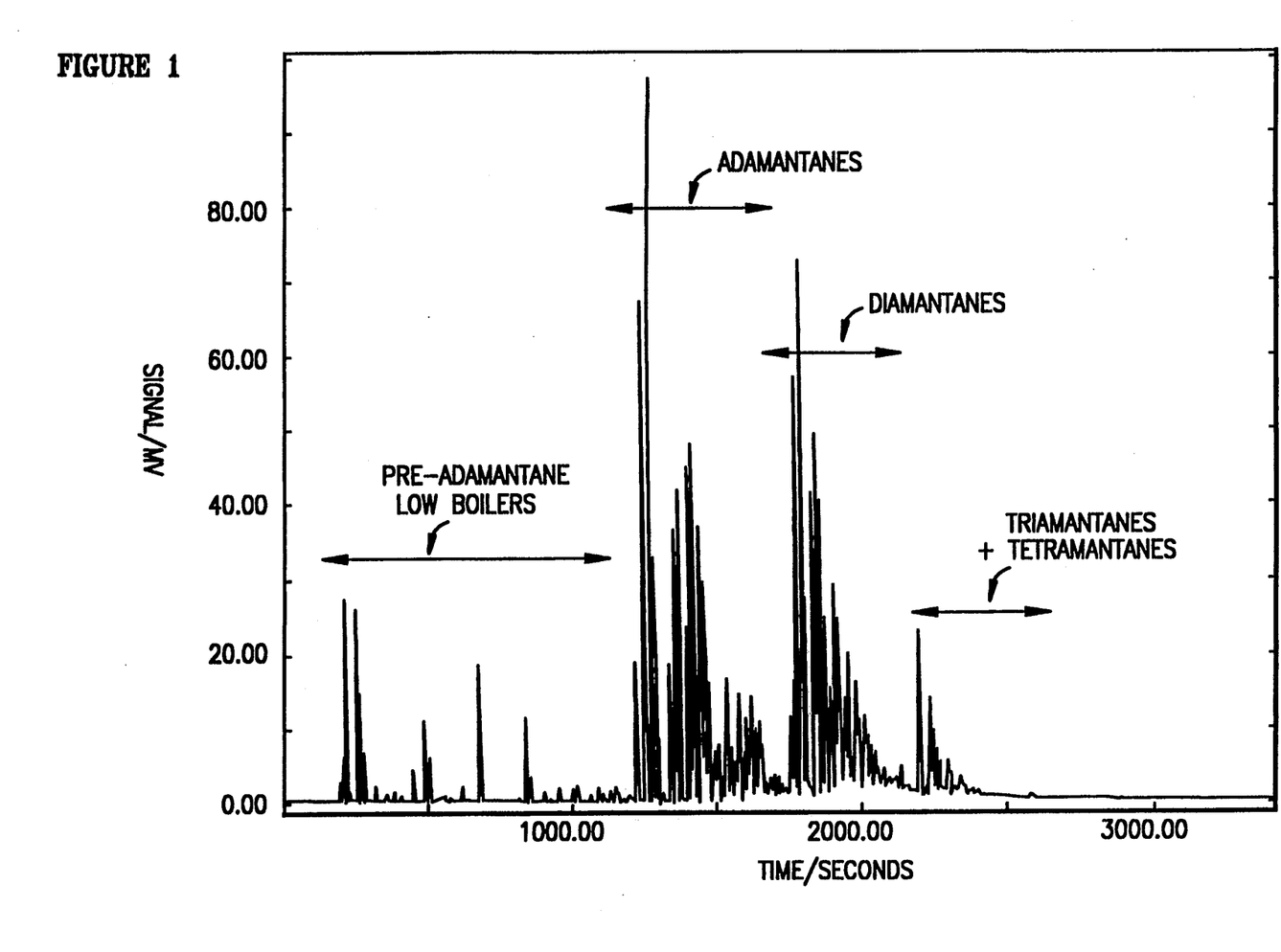
FIG. 1 is a GC trace of the starting diamondoid mixture used as feedstock for the distillation of Example 1.
Figure 2:
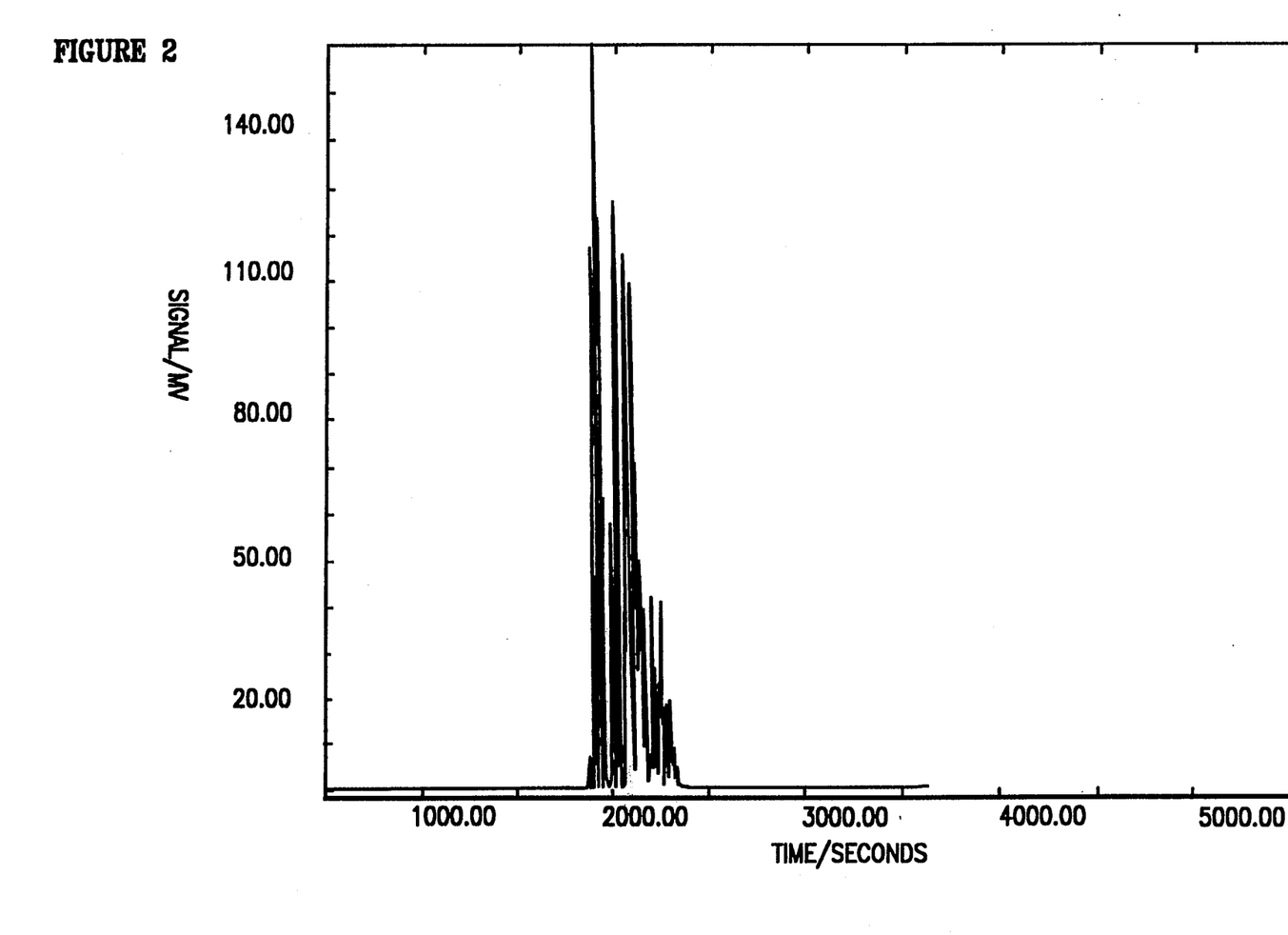
FIG. 2 is a GC trace of the adamantanes-enriched mixture recovered from the distillation of Example 1.
Figure 5:
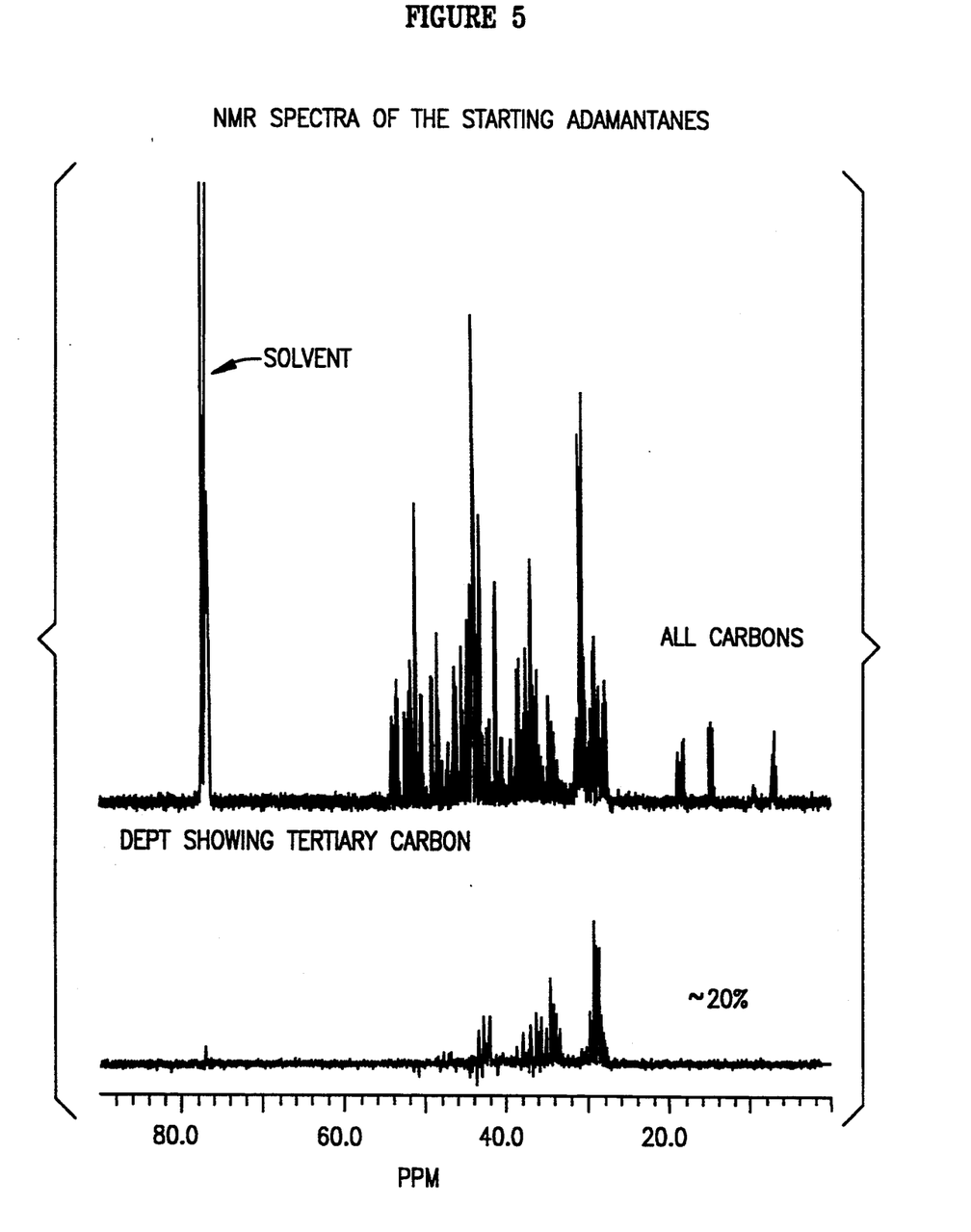
FIG. 5 is an NMR spectrum of the mixture of unsubstituted and alkyl-substituted (especially methyl-substituted) diamondoid compounds described in FIG. 2. The mixture of FIGS. 2 and 5 is useful as a feedstock to produce the mixed per-esterified lubricant base stock of the present invention. The spectrum of FIG. 5 shows the presence of primary and secondary carbons, as well as tertiary and quaternary bridgehead carbons.

Example 1 recovered a mixture of alkyl-substituted adamantanes from a normally liquid mixture of diamondoid compounds using an ASTM D-2887 distillation unit having a column packed with stainless steel saddles. A two-neck flask was used to allow a flow of nitrogen through the material to be distilled. Two thousand grams of the normally liquid diamondoid mixture which had been percolated through activated alumina (see FIG. 1 for a GC trace) were charged into the flask. Nitrogen was passed through the material at the beginning of the distillation at a rate of 20 cc/min. At room temperature, it was observed that by simply bubbling nitrogen through the bottom of the liquid, some of the low boiling constituents were collected in a dry ice/acetone trap. The distillation was carried out at a reflux ratio of 8:1. At atmospheric pressure, a pot temperature of 140°–180° C. and a head temperature of 23°–24° C., a first fraction (114 grams) consisting of 99% low-boiling nondiamondoid material and 1% adamantanes was collected. This fraction was combined with the material in the dry ice/acetone trap as the pre-adamantane fraction. The distillation was continued either at atmospheric or reduced pressure to isolate the adamantanes. Solid adamantane was condensed at the top of the condenser and take-off arm before the liquid substituted adamantanes came over and condensed as liquid. The solid was melted by a heat gun and combined with the liquid. A total of 840 grams of 99%+adamantanes were obtained. FIG. 2 shows a GC trace of this distilled adamantanes-enriched fraction. FIG. 5 is an NMR spectrum of the same fraction.

Example 2

Figure 6:
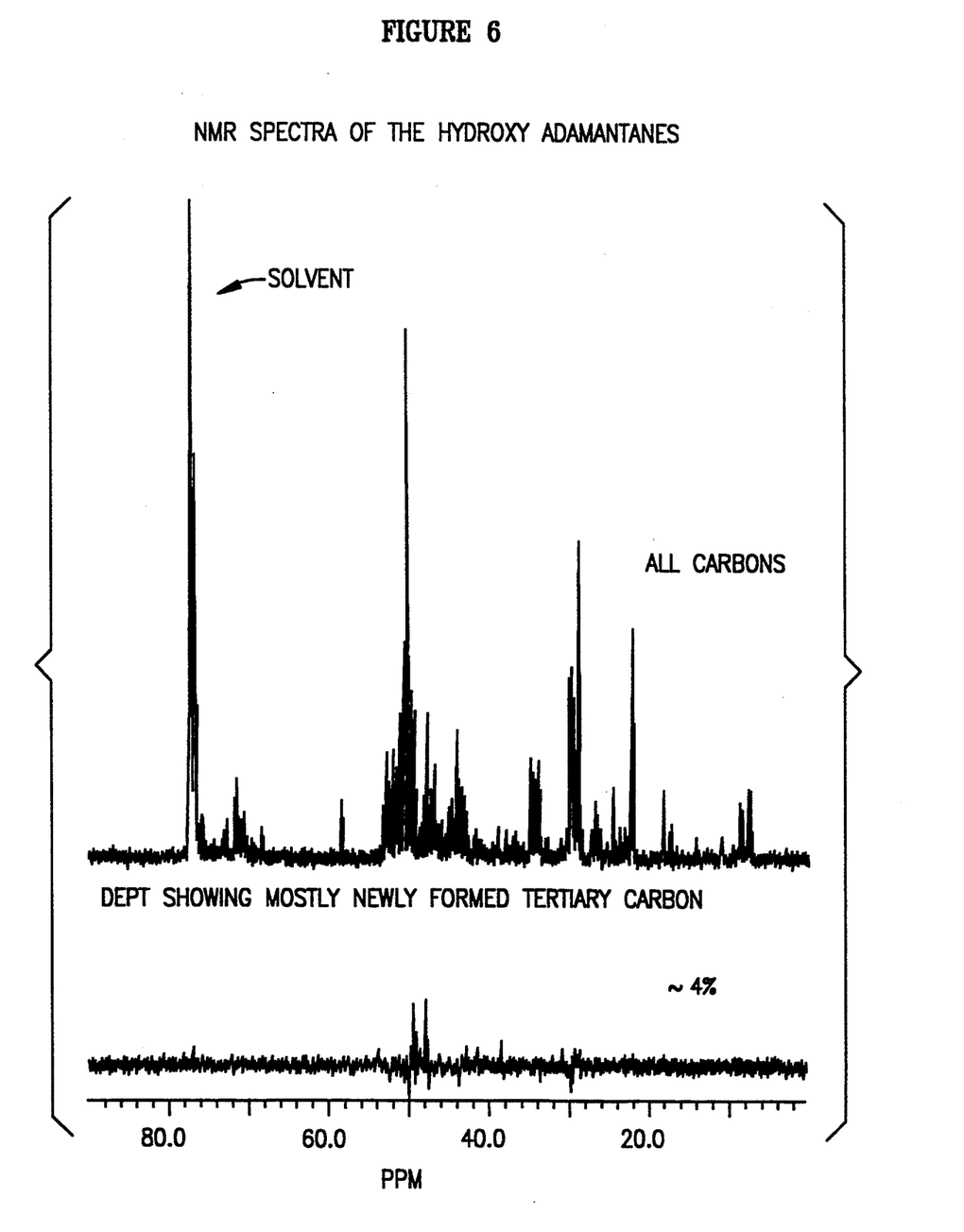
FIG. 6 is an NMR spectrum of the diamondoid mixture of FIG. 5 which has been oxidized or hydroxylated at the bridgeheads. Comparing
Figure 7:
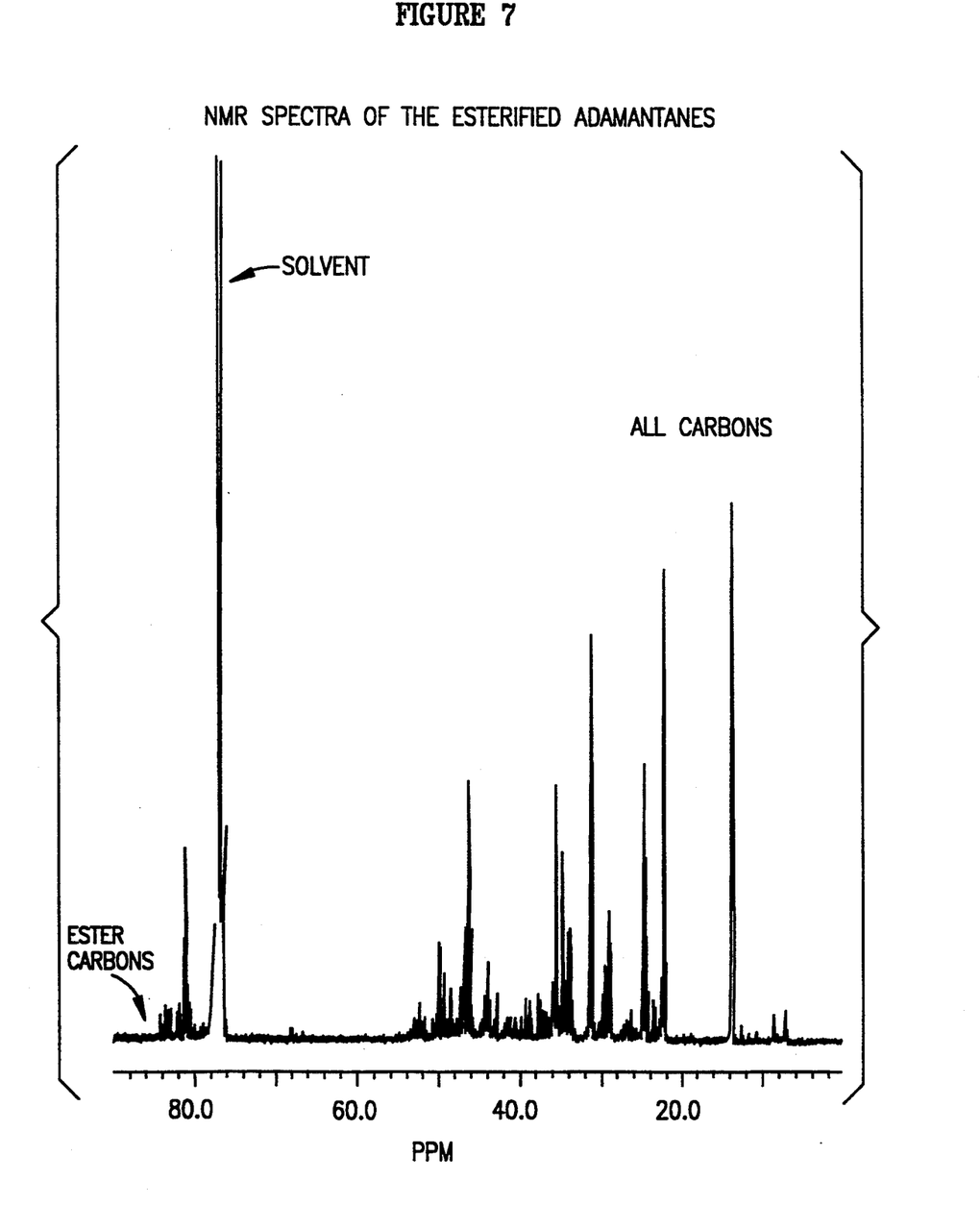
FIG. 7 is an NMR spectrum of the diamondoid mixture of FIG. 6 which has been esterified. Comparing

Example 2 converted the distilled adamantanes-enriched fraction of Example 1 to completely oxidize the bridgehead carbons in the adamantanes to the corresponding hydroxyl products. The NMR spectrum of FIG. 6 shows that the oxidation step of Example 2 produced a minor amount of new tertiary carbons which are believed to have been formed through the oxidation of the secondary carbons in the adamantane molecules.

Figure 3:
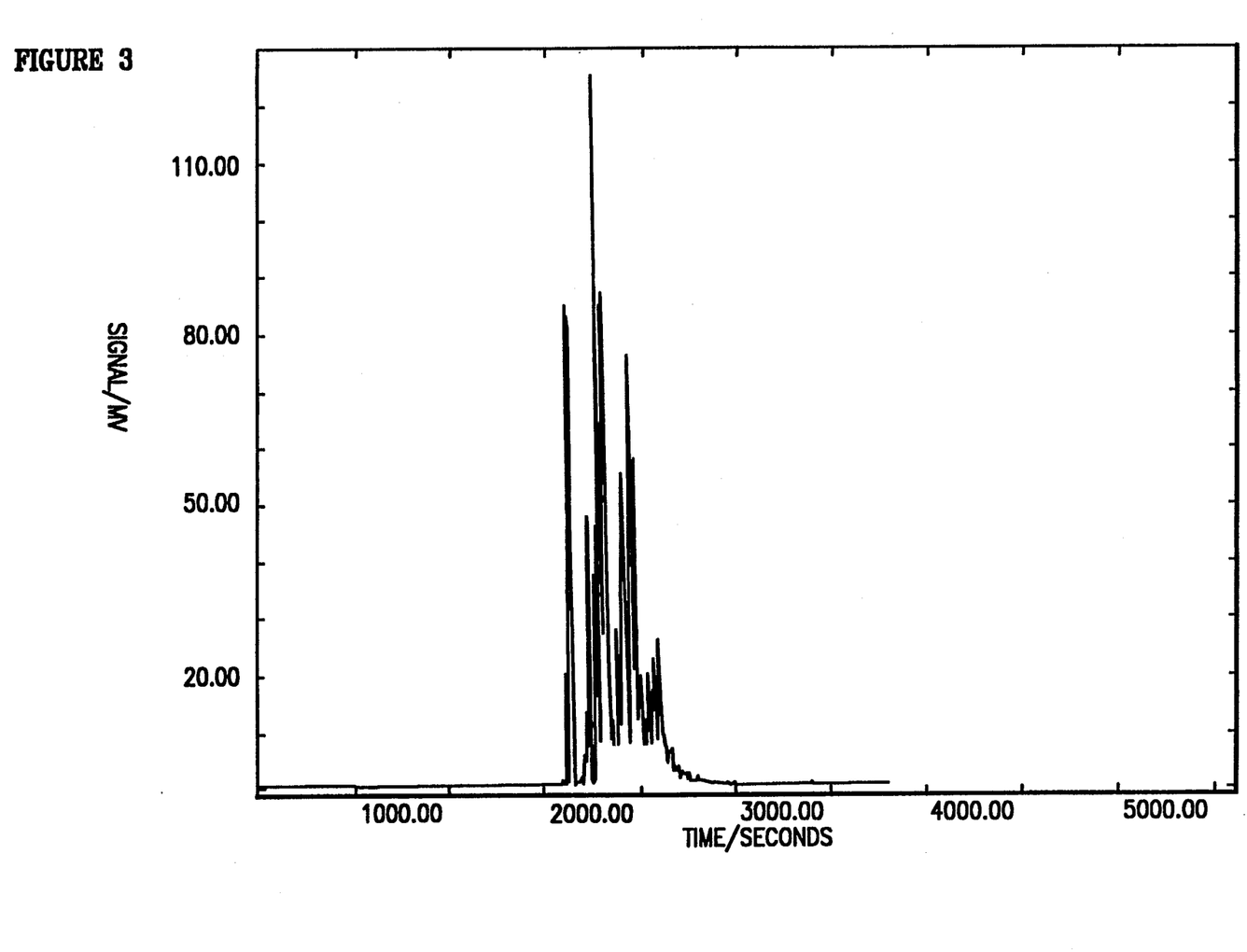
FIG. 3 is a GC trace of the hydroxylated adamantanes product of Example 2.

Into a four-neck flask immersed in a cooling bath and equipped with a low-temperature condenser (−20° C.), an air-driven well-sealed mechanical stirrer (to minimize loss of volatile expensive trifluoroacetone), a solid addition funnel, and a thermocouple, there were added in the following order:

33.8 g of the adamantanes obtained in Example 1, 225 ml dichloromethane, 450 ml double distilled water, 288 g sodium bicarbonate and 300 ml tert.-butyl alcohol. The mixture was cooled to −9° C. with stirring and 150 g trifluoroacetone were added. The temperature rose to 5° C. After the mixture cooled to −10° C., 675 g OXONE brand monopersulfate compound (formula: 2KHSO$_5$.KHSO$_4$K$_2$SO$_4$, purchased from E. I. Du Pont de Nemours and Company, 1007 Market Street, Wilmington, Del., 19898) were added in portions through the solid addition funnel, keeping the reaction temperature between −8° and 0° C. The reaction was not noticeably exothermic during the addition. Near the end of the addition gas evolution was detected in the bubbler connected through the top of the condenser. The reaction mixture was a white paste and was stirred overnight at −2° C. The pot was then connected to a cold receiver through one neck and was warmed gradually to 40° C. to distill off and recover the trifluoroacetone. The pot material was filtered by suction. The filtrate was rotavapped to dryness. A crude product (33.2 g) was obtained. The large amount of solids from the filtration was refluxed in ethanol and filtered. An additional 6.3 g of products were obtained from the ethanol extract. FIG. 3 shows a GC profile of the oxidized products. Comparing FIGS. 2 and 3 indicates that the product has a higher boiling range than the starting material. NMR DEPT (FIG. 5) indicated that essentially all the original tertiary carbons had been converted to quaternary carbons attached to —OH groups, suggesting that the bridgehead positions were fully oxidized to hydroxy compounds.

Example 3

Figure 4:
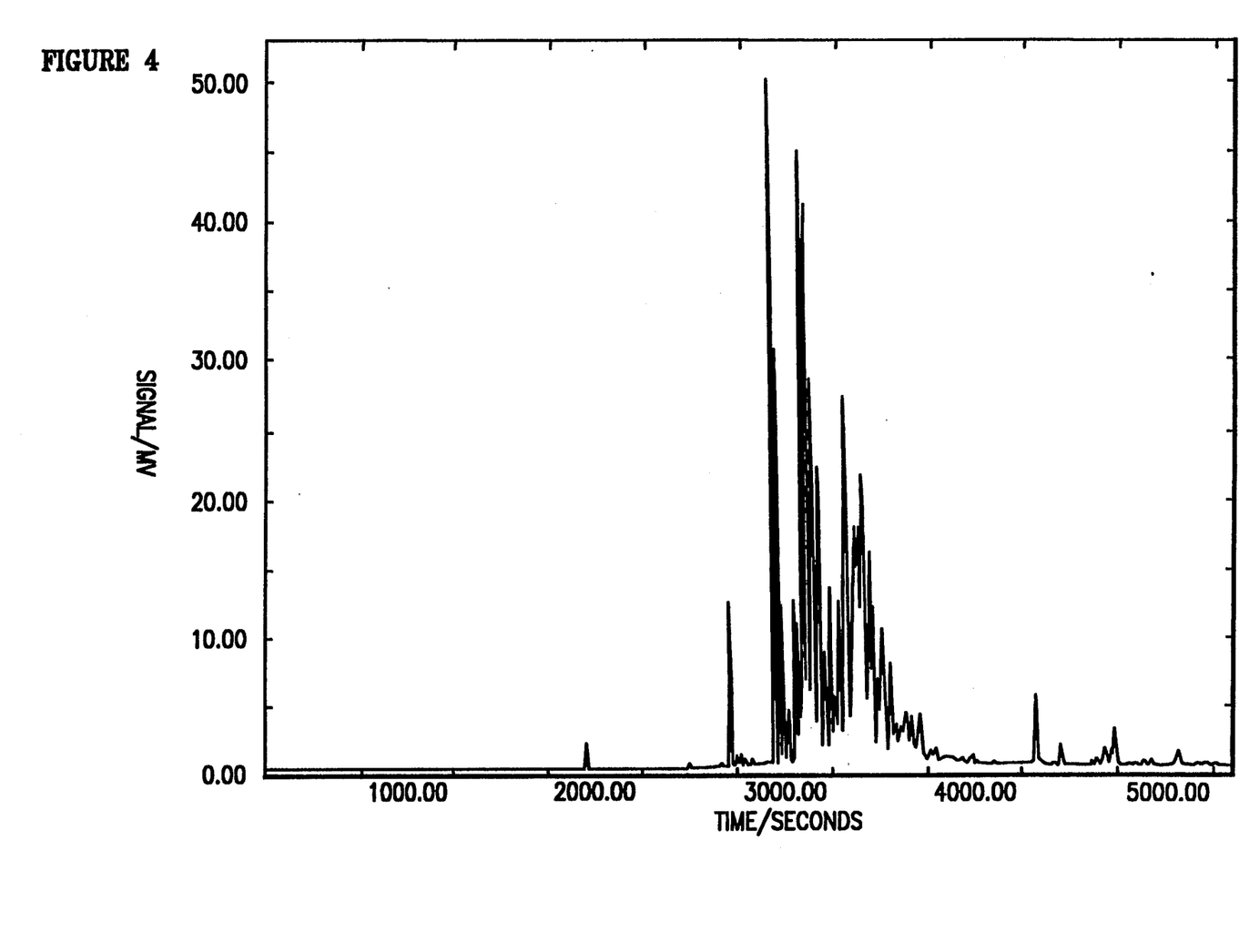
FIG. 4 is a GC trace of the esterified adamantanes product of Example 3.

Example 3 esterified the hydroxyadamantanes of Example 2. The hydroxyadamantanes obtained in Example 2 together with five times their weight of methyl decanoate into a three-neck flask equipped with a condenser with a drying tube attached, a magnetic stirrer, a nitrogen bubbler, and a thermometer. With stirring, 0.05 ml of titanium (IV) isopropoxide (Aldrich) was dropped in, and the reaction mixture was heated to 165° C. with a slow stream of nitrogen bubbling through to keep the reaction under inert atmosphere and to carry out methanol formed in the ester exchange reaction. The esterification was monitored by periodically sampling and analyzing (GC) the reaction mixture. The reaction was judged to be complete when the boiling range distribution of the reaction mixture did not change further. To assure that the reaction was complete, an additional 0.05 ml catalyst was added and the reaction was continued and analyzed. The esterification under these conditions was complete in 48 hours. The mixture was distilled under vacuum, first with a one-foot vacuum jacketed Vigreux column to recover the excess methyl decanoate and to remove the lower boiling esters (<650° C.). The distillation was cooled down and the column was removed, the remainder of the esters was short-path distilled under vacuum. The esters distilled at a pot temperature of 160°–285° C. and a head temperature of 105°–245° C. under a vacuum of 0.3–0.4 Torr. A small amount of black residue containing the catalyst remained in the pot. The distilled esters were pale yellow in color. NMR analysis showed the complete disappearance of the —OH groups accompanied by the appearance of the ester groups. FIG. 4 is a GC profile of the esterified products. FIG. 6 is an NMR spectrum of the esterified products of Example 3. Table III shows the boiling range of the esterified products of Example III.

TABLE III

| Boiling Range of Example 3 Product | | | | | |
|---|---|---|---|---|---|
| wt. % | degrees F. | wt. % | degrees F. | wt. % | degrees F. |
| 0 | 633 | 33 | 744 | 67 | 887 |
| 1 | 702 | 34 | 745 | 68 | 889 |
| 2 | 712 | 35 | 747 | 69 | 891 |
| 3 | 714 | 36 | 749 | 70 | 892 |
| 4 | 716 | 37 | 750 | 71 | 894 |
| 5 | 716 | 38 | 751 | 72 | 895 |
| 6 | 717 | 39 | 753 | 73 | 896 |
| 7 | 718 | 40 | 754 | 74 | 898 |
| 8 | 719 | 41 | 755 | 75 | 899 |
| 9 | 721 | 42 | 757 | 76 | 900 |
| 10 | 723 | 43 | 758 | 77 | 901 |
| 11 | 724 | 44 | 759 | 78 | 903 |
| 12 | 725 | 45 | 760 | 79 | 904 |
| 13 | 726 | 46 | 762 | 80 | 905 |
| 14 | 727 | 47 | 763 | 81 | 906 |
| 15 | 727 | 48 | 764 | 82 | 908 |
| 16 | 728 | 49 | 765 | 83 | 909 |
| 17 | 729 | 50 | 767 | 84 | 910 |
| 18 | 729 | 51 | 769 | 85 | 911 |
| 19 | 730 | 52 | 771 | 86 | 912 |
| 20 | 731 | 53 | 772 | 87 | 913 |
| 21 | 731 | 54 | 776 | 88 | 914 |
| 22 | 732 | 55 | 779 | 89 | 915 |
| 23 | 732 | 56 | 784 | 90 | 916 |
| 24 | 733 | 57 | 800 | 91 | 917 |
| 25 | 733 | 58 | 812 | 92 | 918 |
| 26 | 734 | 59 | 823 | 93 | 920 |
| 27 | 735 | 60 | 833 | 94 | 921 |
| 28 | 735 | 61 | 863 | 95 | 922 |
| 29 | 737 | 62 | 875 | 96 | 923 |
| 30 | 739 | 63 | 879 | 97 | 924 |
| 31 | 740 | 64 | 881 | 98 | 931 |

TABLE III-continued

| Boiling Range of Example 3 Product | | | | | |
|---|---|---|---|---|---|
| wt. % | degrees F. | wt. % | degrees F. | wt. % | degrees F. |
| 32 | 742 | 65 | 883 | 99 | 997 |
|  |  | 66 | 886 | 100 | 1088 |

Example 4

Figure 8A:
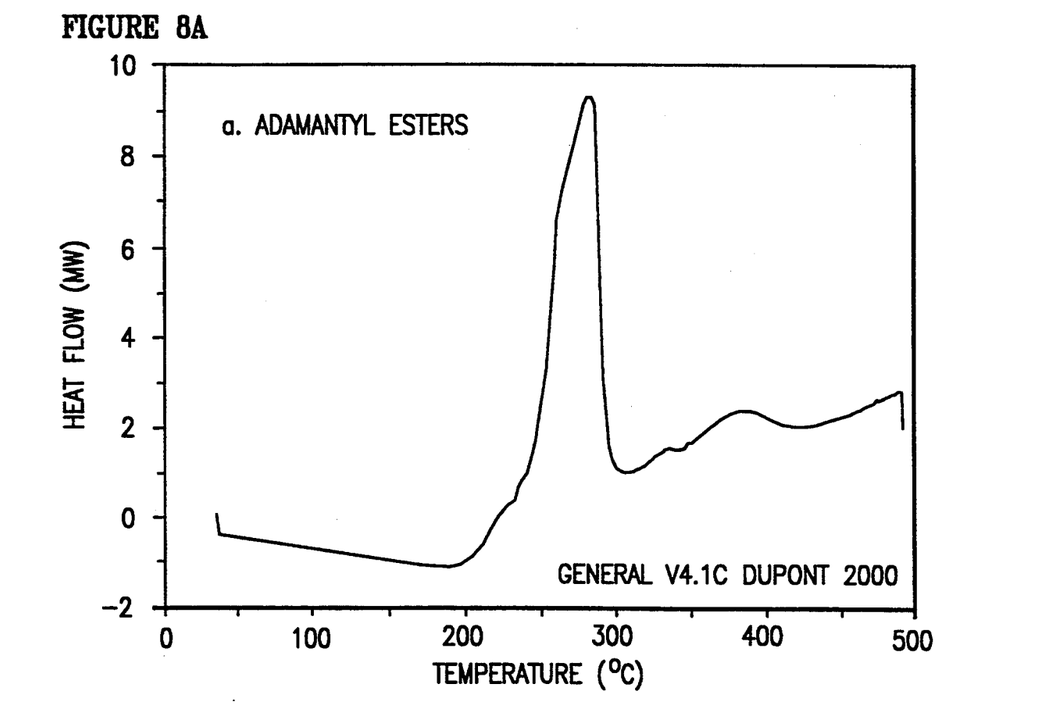
FIG. 8A plots the results of a DSC (Differential Scanning Calorimetry) oxidative stability test of Example 4 which evaluated the adamantyl esters product of Example 3, showing heat flow (mW, the y-axis) as a function of temperature (°C., the x-axis). The exothermic peaks indicate the oxidative decomposition temperature.
Figure 8B:
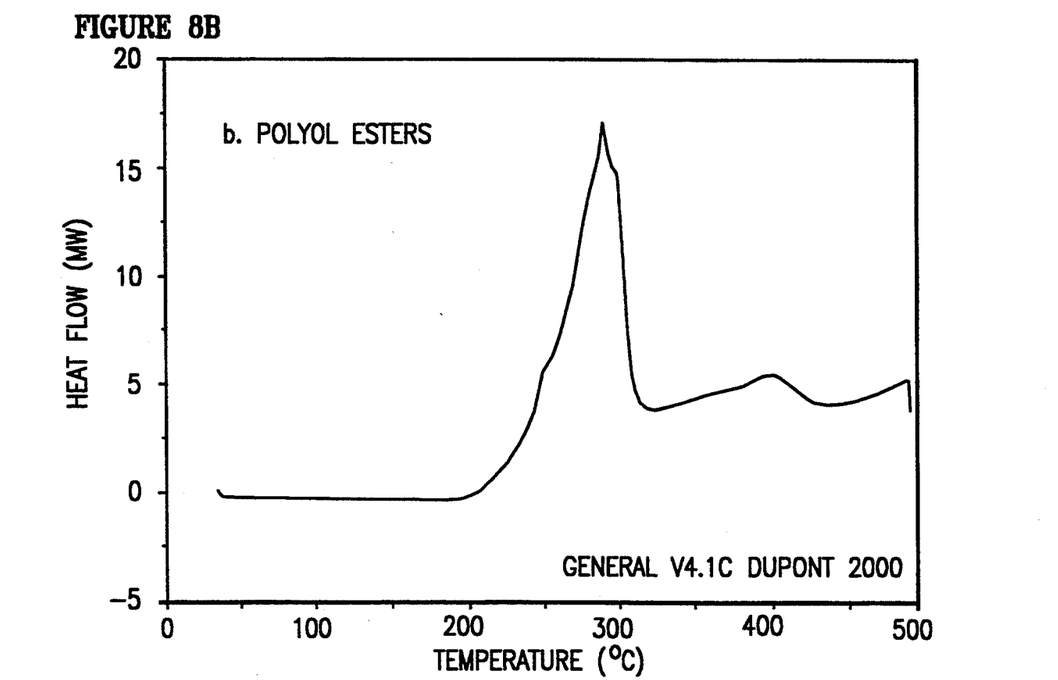
FIG. 8B plots the results of a DSC oxidative stability test of a thermally and oxidatively stable commercial polyol ester-containing jet oil base stock.
Figure 9A:
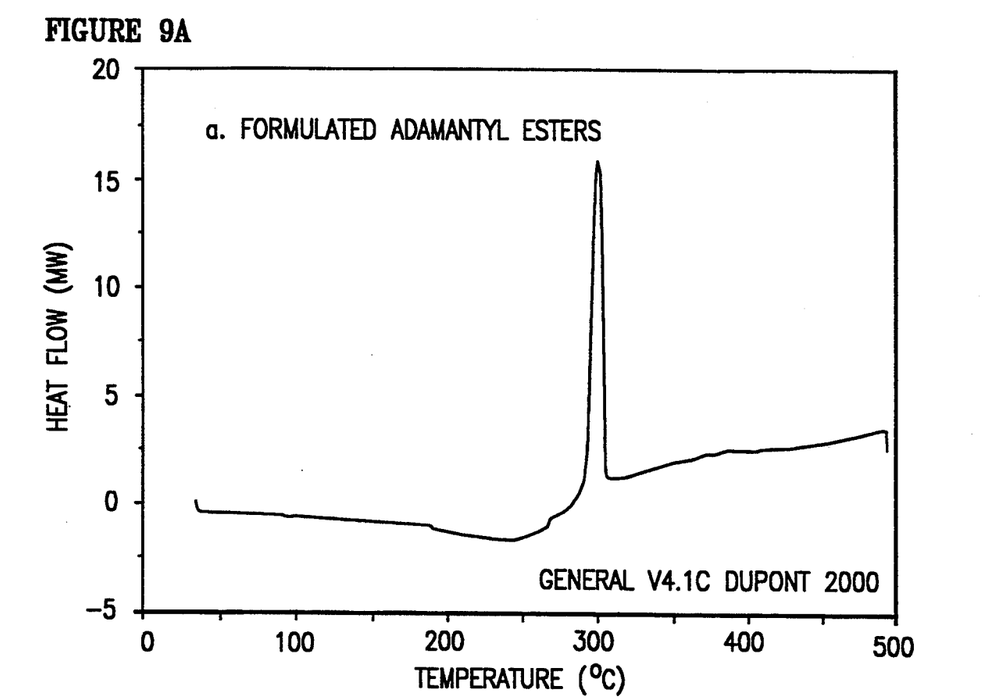
FIG. 9A plots the results of a DSC oxidative stability test of Example 4 which evaluated the adamantyl esters product of Example 3 to which had been added a standard jet oil additive package.
Figure 9B:
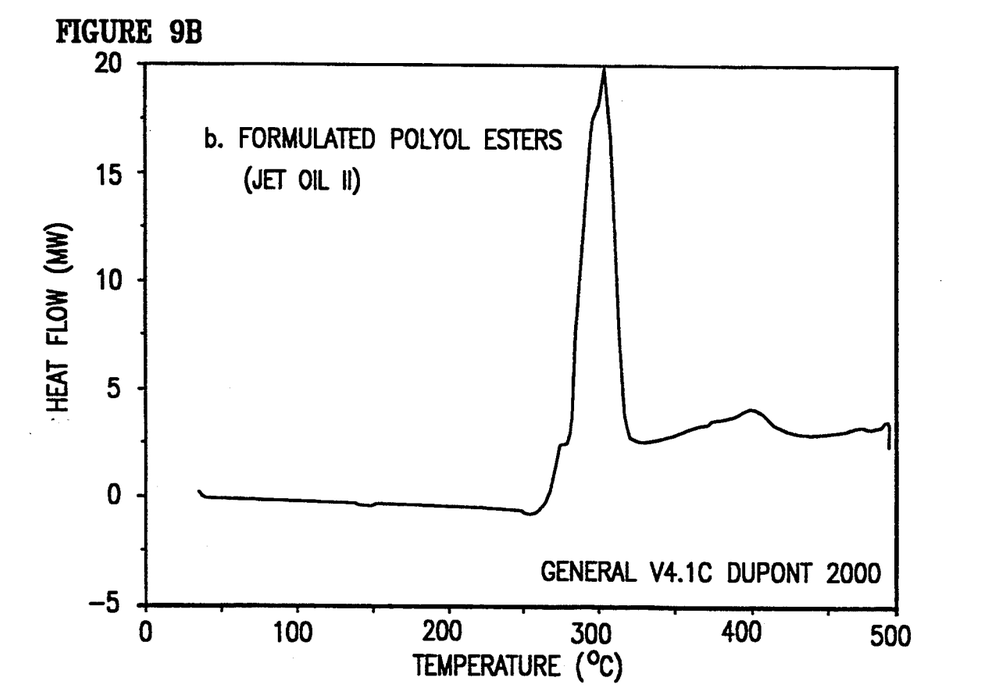
FIG. 9B plots the results of a DSC oxidative stability test of a commercial polyol ester-containing jet oil containing a standard jet oil additive package.

Example 4 evaluated the stability of the esters obtained in Example 3 and a commercial jet oil product. FIGS. 8A and 8B compare the oxidative stability of the ester basestocks by DSC (Differential Scanning Calorimetry). The DSC analyses were conducted with a DSC low pressure cell manufactured by DuPont de Nemours and Company, 1007 Market Street, Wilmington, Del. 19898. DSC data were collected using a Ta Model 2000 computer from TA Instruments, Inc., 109 Lukens Drive, Newcastle, Del. 19720. For a general overview of differential scanning calorimetry, see 2 Kirk-Othmer Encyclopedia of Chemical Technology 611 (3rd ed., 1978). For a more detailed description of differential scanning calorimetry, see Thermal Analyst 2000 Operator's Manual, Version 8.3 (Revision E, 1991) which is available as Product No. 996524.001 from Ta Instruments, Inc. A standard additive package was added to samples of both the commercial base stock and the base stock of Example 3 to compare the oxidative stabilities of the formulated oils. FIGS. 9A and 9B show the results of this comparison, with both products demonstrating good oxidative stability.

Changes and modifications in the specifically described embodiments can be carried out without departing from the scope of the invention which is intended to be limited only by the scope of the appended claims.

What is claimed is:

1. A composition comprising Formula I as shown below and at least one selected from the group consisting of Formulae II, III, IV, and V as shown below:

Formula I

Formula II

Formula III

Formula IV

Formula V wherein $R_1$, $R_2$, $R_3$, and $R_4$ are the same or different, and comprise alkyl groups containing no tertiary carbon and having from 4 to about 15 carbon atoms.

2. The composition of claim 1 wherein $R_1$, $R_2$, $R_3$, and $R_4$ comprise from about 5 to about 12 carbon atoms.

3. The composition of claim 2 wherein $R_1$, $R_2$, $R_3$, and $R_4$ comprise from about 6 to about 10 carbon atoms.

4. The composition of claim 1 wherein $R_1$, $R_2$, $R_3$, and $R_4$ are the same.

5. The composition of claim 1 wherein $R_1$, $R_2$, $R_3$, and $R_4$ comprise alkyl groups of two, three, or four different chain lengths.

6. A mixture comprising at least two different compounds of claim 1.

7. A mixture comprising at least two different compounds of claim 2.

8. A mixture comprising at least two different compounds of claim 3.

9. A lubricant comprising the composition of claim 1 and at least one selected from the group consisting of oxidation inhibitors, antiwear agents including extreme-pressure antiwear additives, viscosity index improvers, and coantioxidants.

10. The lubricant of claim 8 further wherein said oxidation inhibitors, antiwear agents including extreme-pressure antiwear additives, viscosity index improvers, and coantioxidants are selected from the group consisting of phenates, sulfonates, succinimides, and zinc dialkyl or diaryl dithiophosphates.

11. The lubricant of claims 9 further characterized by a viscosity range of from about 45 SSU at 100° F. to about 6000 SSU at 100° F.

12. The lubricant of claim 11 further characterized by a viscosity range of from about 50 to about 250 SSU at 210° F.

13. A grease comprising the composition of claim 1 and at least one thickening or gelling agent.

14. The grease of claim 13 wherein said thickening or gelling agent is selected from the group consisting of metal salts and metal soaps.

15. The grease of claim 14 wherein said metal salts and metal soaps are selected from the group consisting of calcium stearates, lithium stearates, and hydroxystearates.

16. The grease of claim 12 wherein said thickening or gelling agent is a non-soap thickeners.

17. The grease of claim 6 wherein said non-soap thickener is selected from the group consisting of surface-modified clays and silicas, aryl ureas, calcium complexes and similar materials.

18. A method for making a per-esterified adamantane compound comprising the steps of fully hydroxylating all tertiary carbons of the adamantane compound including the bridgehead positions of the adamantane compound in the presence of a dioxirane and esterifying the hydroxyl groups in the presence of an esterification catalyst to form a per-esterified adamantane compound containing essentially no tertiary carbon atoms.

19. The method of claim 18 wherein the dioxirane is methyl (1,1,1-trifluoromethyl) dioxirane.

20. The method of claim 18 wherein the dioxirane is formed in situ from 1,1,1-trifluoroacetone and inorganic persulfate.

21. The method of claim 20 wherein the inorganic persulfate is potassium hydrogen persulfate.

22. The method of claim 18 wherein said esterification catalyst is a titanium (IV) alkoxide.

23. The method of claim 22 wherein said esterification catalyst is titanium (IV) isopropoxide.

24. The method of claim 18 wherein said esterification agent is selected from the group consisting of alkyl alkanoates containing no tertiary carbon.

25. The method of claim 24 wherein the esterification agent is selected from the group consisting of methyl hexanoate, methyl decanoate, or methyl trimethylacetate.

26. A composition having the structure of Formula I as shown below:

Formula I wherein $R_1$, $R_2$, $R_3$, and $R_4$ are the same or different, and comprise alkyl groups containing no tertiary carbon and having from 4 to about 15 carbon atoms.

27. The composition of claim 26 wherein $R_1$, $R_2$, $R_3$, and $R_4$ comprise from about 5 to about 12 carbon atoms.

28. The composition of claim 27 wherein $R_1$, $R_2$, $R_3$, and $R_4$ comprise from about 6 to about 10 carbon atoms.

29. The composition of claim 26 wherein $R_1$, $R_2$, $R_3$, and $R_4$ are the same.

30. The composition of claim 26 wherein $R_1$, $R_2$, $R_3$, and $R_4$ comprise alkyl groups of two, three, or four different chain lengths.

31. A method for making a per-esterified adamantane compound comprising the steps of fully hydroxylating all tertiary carbons of the adamantane compound including the bridgehead positions of the adamantane compound in the presence of dioxirane and esterifying the hydroxyl groups in the presence of a titanium alkoxide esterification catalyst to form a per-esterified adamantane compound containing essentially no tertiary carbon atoms.

32. The method of claim 31 wherein the dioxirane is methyl (1,1,1-trifluoromethyl) dioxirane.

33. The method of claim 32 wherein the dioxirane is formed in situ from 1,1,1-trifluoroacetone and inorganic persulfate.

34. The method of claim 33 wherein the inorganic persulfate is potassium hydrogen persulfate.

35. The method of claim 31 wherein said esterification catalyst is a titanium (IV) alkoxide.

36. The method of claim 35 wherein said esterification catalyst is titanium (IV) isopropoxide.

37. The method of claim 31 wherein said esterification agent is selected from the group consisting of alkyl alkanoates containing no tertiary carbon.

38. The method of claim 24 wherein the esterification agent is selected from the group consisting of methylhexanoate, methyl decanoate, or methyl trimethylacetate.

* * * * *